United States Patent [19]
Cheong et al.

[11] Patent Number: 6,123,958
[45] Date of Patent: Sep. 26, 2000

[54] WEB DRESSING AND METHOD FOR ITS PRODUCTION

[75] Inventors: Catherine L. Cheong, Burnley; Michelle Delbono, Earby, both of United Kingdom

[73] Assignee: Johnson & Johnson Medical, Inc., Arlington, Tex.

[21] Appl. No.: 08/987,752

[22] Filed: Dec. 9, 1997

Related U.S. Application Data

[63] Continuation of application No. 07/942,568, Sep. 9, 1992, abandoned.

[30] Foreign Application Priority Data

Oct. 9, 1991 [GB] United Kingdom .................... 9119287
Feb. 4, 1992 [GB] United Kingdom .................... 9207239

[51] Int. Cl.[7] ...................................................... A61F 13/02
[52] U.S. Cl. ............................................ 424/443; 424/445
[58] Field of Search ..................................... 424/445, 443

[56] References Cited

U.S. PATENT DOCUMENTS

| | | | |
|---|---|---|---|
| 3,876,771 | 4/1975 | Denner | 424/78 |
| 4,524,064 | 6/1985 | Nambu | 424/81 |
| 4,588,400 | 5/1986 | Ring | 604/304 |
| 4,599,209 | 7/1986 | Dauntzenberg | 264/7 |
| 4,838,253 | 6/1989 | Brassington | 128/156 |
| 4,921,704 | 5/1990 | Fabo | 424/446 |
| 5,156,601 | 10/1992 | Lorenz | 604/307 |

FOREIGN PATENT DOCUMENTS

| | | | |
|---|---|---|---|
| 0174849 | 3/1986 | European Pat. Off. | C08F 2/46 |
| 2043668 | 10/1980 | United Kingdom | C08B 31/10 |
| 2220417 | 1/1990 | United Kingdom | C08B 37/08 |
| 92/16245 | 10/1992 | WIPO | A61L 25/00 |

*Primary Examiner*—Thurman K. Page
*Assistant Examiner*—B. Fubara
*Attorney, Agent, or Firm*—Andrew C. Farmer; Theodore Shatynski

[57] ABSTRACT

The present invention provides a dressing consisting of a non-reinforced, apertured gel web, wherein the gel is substantially anhydrous and comprises a water-soluble, polysaccharide- or cellulosic-polymer and a humectant, for use in treating burns. The present invention also provides a method for making the dressing.

11 Claims, 1 Drawing Sheet

WEB DRESSING AND METHOD FOR ITS PRODUCTION

This application is a continuation of U.S. application Ser. No. 07/942,568 filed Sep. 9, 1992, now abandoned and which is hereby incorporated by reference.

The present invention relates to a web dressing and to a method for its production. In particular, it relates to a web dressing for use on burns and ulcers, especially ones which are producing wound exudate.

A wide variety of dressings are known for treating all kinds of wounds. They come in a variety of shapes and constructions. The most commonly available dressing comprises a backing sheet, one side of which is covered with an adhesive. An absorbent pad is located on the adhesive layer, generally in the centre of the backing sheet. The backing sheet may be air-permeable or air-impermeable and, if air permeable, may be liquid permeable or liquid impermeable. Such dressings generally have one or two release sheets covering the exposed areas of the adhesive layer to facilitate storage and use.

Such common dressings are generally used to treat minor cuts and abrasions. However, they are not generally suitable for use on more major wounds such as burns or ulcers. These types of wound tend to produce significant quantities of exudate, which cannot be absorbed by the absorbent pad on the common dressing. Moreover, as the exudate dries out, or as a scab forms over the wound, the dried exudate or the scab forms around the fibers in the absorbent pad. This makes it difficult, if not impossible, to remove the dressing without causing damage to the wound.

This problem can be exacerbated by the adhesive layer being present. This can stick not only to the skin adjacent the wound but also to the wound itself. This increases the difficulty of removing the dressing without damaging the wound.

There have therefore been many proposals for producing dressings which can be used to treat exuding wounds, such as burns and ulcers, without the problem of the dressing adhering to the wound.

In particular, U.S. Pat. No. 4,921,704 describes a dressing comprising an apertured fibrous web, the fibres in the web being encapsulated in a hydrophobic, tacky resin. The fibres are encapsulated in order to prevent them from coming into contact with the healing wound. This web dressing is designed so that any exudate from the wound will pass through the dressing and be absorbed by an absorbent pad placed on top of the dressing. Nonetheless, the web dressing may still become stuck to the wound. For instance, movement of the dressing may cause the fibres to protrude through the dressing and into the wound. These fibres may become stuck in drying exudate or in a forming scab. In any event, it is necessary to remove the web dressing following treatment. There are a number of other disadvantages of the web dressings described in U.S. Pat. No. 4,921,704.

Our copending UK patent application No. UK-A-9102089.1 describes an improved web dressing comprising an apertured fibrous web, the fibres being encapsulated in a hydrophilic, tacky resin. This web dressing is an improvement over the dressings shown in U.S. Pat. No. 4,921,704 for the reasons set out in UK-A-9102089.1. However, it is still necessary to remove the dressing from a wound once healing has progressed to the required degree.

For treating wounds such as ulcers and, in particular, burns, a dressing desirably has a number of properties. It should not be adherent to the wound. It should be highly conformable so that it can effectively cover the wound and it should retain a moist feel. Especially for burns, which are hot wounds, it should have a cooling effect. Preferably, the dressing should be able to carry medicaments or additives in order to aid wound healing. None of the dressings which are currently available have all of these properties.

It has been proposed that films of hydrogel materials should be used to treat ulcers and burns. These hydrogel materials are very expensive, are not very conformable and are water-insoluble. Moreover, they tend to dry out on use, leaving a pellicle of material stuck to the wound. Thus, although these films may have some cooling effect, are initially non-adherent and are absorbent, they have disadvantages which reduce their usefulness in treating ulcers and burns.

It is therefore an object of the present invention to provide a dressing which is an improvement over the prior art dressings and which is particularly suitable for treating ulcers and burns.

According to the present invention, there is provided a dressing consisting of a non-reinforced, apertured gel web, wherein the gel is substantially anhydrous and comprises a water-soluble, polysaccharide- or cellulosic-polymer and a humectant.

Preferably, the dressing is lightly tacky, although, if desired, it may be non-tacky.

The apertures in the dressing may be of any desired shape, such as circular or square. Preferably the apertures are square. Generally, the diameter or width of each aperture is from 0.5 to 5.0 mm and preferably is from 1.0 to 3.0 mm. The width of the gel between the apertures is generally between 0.5 and 5.0 mm and preferably is from 1.0 to 3.0 mm. The thickness of the web will generally be from 0.5 to 5.0 mm and will preferably be from 1.0 to 3.0 mm.

It will be understood that the dressing of the present invention need not be uniform. Thus, the apertures may be of a variety of shapes and sizes and the width of the gel between the apertures may vary. In particular, it is envisaged that the depth of the gel between the apertures may vary.

For instance, each element of the web may have a U-shaped or a V-shaped cross section. This is of particular advantage where the dressing is tacky in that it provides a gel web having one relatively non-tacky surface, comprising the arms of the U- or V-shaped web elements, and one relatively tacky surface, comprising the bases of the U- or V-shaped web elements. In use, the non-tacky surface can be placed on the wound and will not stick thereto. The tacky surface will thus be remote from the wound. An absorbent pad can be stuck onto the tacky surface, but is kept remote from the wound by the dressing. The fact that the non-tacky surface is in contact with the wound further reduces the possibility that the dressing will adhere to the wound.

Alternatively, the dressing can be used with the tacky side adjacent the wound and the relatively non-tacky side having an absorbent pad thereon. In this case, as the pad-contacting surface is at best only lightly tacky, the absorbent pad can readily be removed from the dressing when it is saturated.

Suitable water soluble polymers for use in the dressing of the present invention include, but are not limited to, hydroxyethylcelluloses, carboxymethyl celluloses and water soluble alginates such as sodium or potassium alginate. The polymers may be used alone or in combinations.

Humectants are low molecular weight, hydrophilic materials. Suitable humectants include glycerol, sorbitol, propylene glycol, low molecular weight polyethylene glycols and low molecular weight polypropylene glycols. If a polymeric humectant is used, preferably it has a molecular weight of at least 200 in order to reduce any tendency for it to leach out of the dressing in use. The humectants may be used alone or in combinations. Sorbitol is particularly useful in combination with other humectants. A particularly suitable combination comprises a mixture of glycerol and propylene glycol.

Preferably, the gel comprises from 2 to 8 parts by weight of humectant or mixture of humectants, for each part by weight of water-soluble polymer. As the amount of humectant increases, so does the tackiness of the dressing. Most preferably, the gel comprises from 5 to 7 parts of humectant (s) for each part by weight of water-soluble polymer.

Preferably, the gel further comprises a medicament or an additive. Suitable medicaments or additives include for example: chlorhexidine or one of its derivatives, such as chlorhexidine hydrochloride, acetate or gluconate; povidone-iodine; a quaternary ammonium salt such as cetyl pyridinium chloride; silver sulphur diazine; a local anaesthetic; a growth factor; an enzyme: a glycosaminoglycan; or a matrix protein. Suitable glycosaminoglycans include hyaluronic acid, chondroitin 4 sulphate, chondroitin 6 sulphate, keratan sulphate and heparan sulphate. Suitable matrix proteins include fibronectin, laminin and collagen.

Such medicaments or additives may be present to promote or aid wound healing or to prevent or treat infections which may otherwise substantially interfere with the wound healing process.

If necessary, the gel further comprises a preservative to prevent microbial growth during storage of the product. However, in general, the dressing will be packaged in a hermetically sealed container and sterilized, for instance using radiation. In this case, a preservative will be unnecessary.

If desired, the dressing may contain a buffering agent. Generally, wounds are naturally acidic. However, an acidic environment may not be conducive to wound healing or may interfere with the operation of a medicament or additive added to the dressing. In such cases it may be desirable to incorporate in the gel a buffering agent which, when released into the wound, raises the pH of the wound, preferably so that the wound is at the optimum value for the action of the medicament or additive or for promoting wound healing. Advantageously, the buffering agent is a biocompatible buffering agent, such as an amino acid-based agent, a Tris buffer or one of Good's buffers.

Although it is preferred that the gel is completely anhydrous, it will be appreciated that it will be difficult to achieve this in practice since all the major components in the gel are hydrophilic. Nonetheless, the gel should be as anhydrous as is practically possible.

The gel may contain a minor amount of water-insoluble materials so long as these are not in fibrous form or are convertible to a water soluble form by the action of the wound exudate or by washing with saline. For instance, if the water soluble polymer is sodium or potassium alginate, it may be desirable to add a minor proportion of calcium alginate. Sodium alginate is water soluble and produces a pliable gel, but is not a haemostat. Calcium alginate, on the other hand, is water-insoluble, produces a less pliable gel but is a haemostat. Thus, a mixture of sodium and calcium alginates will provide a dressing having a good balance of properties.

The apertured nature of the dressing of the present invention enables wound exudate to pass therethrough. An absorbent pad may be place on the side of the dressing remote from the wound in order to absorb such exudate.

However, in cases where there are only small amounts of exudate, it will be unnecessary to use an absorbent pad as the dressing itself will be able to absorb the exudate. This absorption will assist in the dissolution of the dressing.

The dressing of the present invention is non-adherent, since it is at best only lightly tacky, and thus can be removed, if necessary, without causing any discomfort to the patient or any damage to the wound. However, it is not necessary to remove the present gel web dressing from the wound. Since all the major components in the web are water-soluble, the dressing may dissolve in the wound exudate or may be dissolved by applying water or saline to the wound.

Thus, where the dressing is used to treat a highly exuding wound, although the exudate may block the holes in the web, it will also dissolve the web, thus allowing the exudate to reach and be absorbed by the absorbent pad. The absorbent pad in this case will not stick because of the copious amount of exudate and the effect of the humectant dissolved out of the dressing.

Where the dressing is used to treat a wound which is not producing much exudate, the dressing will remain substantially intact, thus keeping the absorbent pad away from the wound but allowing the exudate to pass through to the absorbent pad. The dressing can then be removed by irrigation, which dissolves the dressing and allows complete removal of all materials placed on the wound.

Where a lightly tacky dressing is used to treat a nearly dry wound, the dressing will tack gently to surrounding skin and will have a soothing effect on the area around the wound. The dressing will not stick to the wound and can be lifted off, or removed by irrigation if necessary.

These are particular advantages of the dressing of the present invention.

The dressing of the present invention also has the advantage that it cannot dry out. Moreover, due to the hydrophilic nature of its major components, it generally feels moist to the touch. While in place on a wound, the dressing will retain its flexibility and moist feel.

It has surprisingly been discovered that, although the dressing of the present invention does not contain water, its application to skin has a cooling effect, thus making it particularly suitable for use in treating burn patients. It can readily be made in large sheet sizes which are particularly suitable for treating large scale burns.

In preferred form, the dressing of the present invention is double-sided, in that it has one relatively tacky and one relatively non-tacky surface. This is a considerable advantage for the reasons set forth above.

It can thus be seen that the dressing of the present invention is an improvement over known wound dressings, especially for use in treating burns.

Preferably, the dressing of the present invention is placed between two sheets of release paper and sealed within a water- and bacteria-impermeable pouch. The pouch and the contents are then sterilised, preferably using gamma irradiation. It is envisaged that other packing procedures may be adopted to provide the dressing of the present invention in sterile form for use.

According to a second aspect of the present invention, there is provided a method for producing a non-reinforced, apertured dressing which comprises:

preparing an aqueous solution comprising a water-soluble, polysaccharide or cellulosic polymer and a humectant;

applying the solution to a mould comprising a pattern of interconnected grooves surrounding a plurality of upstanding bosses; and drying the solution in the mould to form the dressing.

Preferably, the process is adapted to produce a dressing according to tile first aspect of the invention.

Preferably, the solution is dried by placing the mould in a conventional heated oven, a fan assisted oven or a microwave oven. The drying time will depend on the type of oven used and the temperature or power of the oven. For instance, for a wet weight of gel-forming material of about 7.5 g, the following conditions are suitable.

| Oven | Temperature | Time (mins) |
| --- | --- | --- |
| Conventional | 60° C. | 60–100 |
| Conventional | 100° C. | 20–40 |
| Fan-assisted | 60° C. | 30–50 |
| Fan-assisted | 140° C. | 3–7 |
| 650W Microwave | — | 2–4 |

The skilled person will readily be able to determine suitable drying conditions based on the above guidelines, using only routine trial and error experimentation.

If desired, the surfaces of the grooves may have a non-stick coating thereon to facilitate removal of the dressing from the mould. If the grooves are so coated, the solution will shrink evenly as it is dried, thus producing a dressing of substantially constant depth.

Alternatively, the grooves may remain uncoated and the material from which the mould is made may be selected so that it has a degree of affinity for the polymer in the solution. In this case, the solution as it dries will tend to adhere to the surfaces of the grooves, thus producing a dressing having a non-uniform depth. For instance, if the grooves are generally square in cross-section, the resulting dressing will have U-shaped elements between each aperture.

Alternatively, if the grooves are V-shaped in cross-section, the resulting dressing will have V-shaped elements between each aperture.

The mould may be made from any suitable material, such as aluminium, stainless steel or another metal alloy, which may if desired be coated with a release layer such as a fluorocarbon polymer or a silicone polymer.

Alternatively, the mould may be made from a flexible plastics material, such as a silicone rubber. This will be useful in a continuous process for the production of the dressing. The mould may be in the form of a continuous belt to one end of which is applied the solution. At the other end of the belt, the dried dressing is removed from the mould. In between the ends, the belt will pass through a heating zone wherein the solution is dried. The heating may be carried out using infra-red, dielectric or microwave heaters or a conventional or fan-assisted oven.

After removal of the dressing from the mould, it may be placed between two release sheets, if necessary cut to size, placed in a pouch and sterilised.

The present invention will now be described by way of example only with reference to the accompanying drawings.

FIRST PRODUCTION PROCESS

Figure 1A:
FIGS. 1a to 1d show the changing form of a product during the first production process described below.

An aluminium mould was prepared by providing two orthogonal sets of parallel grooves in the surface of a plate of aluminium. The grooves were blocked off at the edges of the plate. The grooves were square in cross-section and were 2.00 mm in width. The distance between each adjacent pair of grooves was 2.00 mm. Thus, the mould comprises a mesh of grooves surrounding bosses which were 2.00 mm square. The depth of each groove was 2.00 mm. A cross-section of the mould is shown in FIG. 1a.

11 g of glycerol and 4 g of propylene glycol were mixed together. To this mixture was added 6 g of hydroxyethyl cellulose (Natrosol 250 HX-Pharm supplied by Aqualon (U.K.) Limited having an average molecular weight of approximately 1.5 MD and a degree of substitution of 2.5 molecules per glucose unit). The components were mixed together using a spatula. To this mixture was added 79 g of water. Mixing with a spatula was continued until a homogeneous solution was produced.

Figure 1B:

The solution was poured onto the mould to fill the grooves. Excess material was scraped off. Due to surface tension effects, the solution formed a concave meniscus. The mould containing the solution is shown in cross section in FIG. 1b.

Figure 1C:

The mould containing the solution was then placed in a circulating air oven at a temperature of 60° C. for 80 minutes until a substantially anhydrous gel was formed. Due to surface tension effects, the solution as it dried clung to the walls of the grooves. The elements of the dressing therefore had a substantially U-shaped cross section, as shown in FIG. 1c.

Figure 1D:
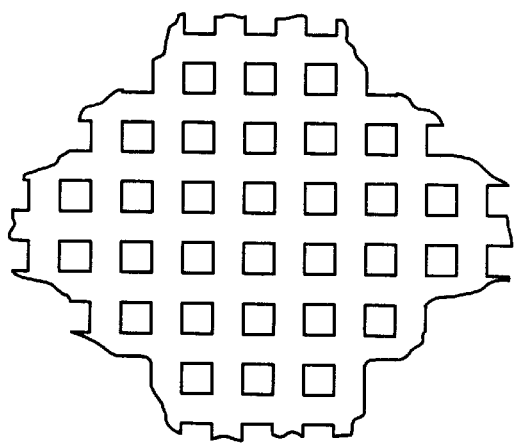

The dressing was then removed from the mould. A plan view of the dressing is shown in FIG. 1d. The dressing was placed between two sheets of release paper, sealed in a pouch and sterilised using gamma irradiation.

SECOND PRODUCTION EXAMPLE

Figure 2A:
FIGS. 2a to 2d show an alternative changing form of a product during the second production process described below.

An aluminium mould was prepared as described for the first production example except that the grooves were V-shaped in cross section. The grooves had a width at the top of 2 mm and a depth of 2 mm. A cross section of the mould is shown in FIG. 2a.

Figure 2B:
Figure 2C:
Figure 2D:
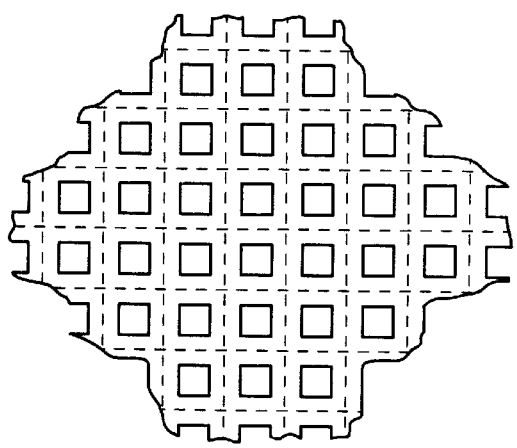

A homogeneous solution containing glycerol, propylene, glycol, hydroxyethyl cellulose and water was produced as described in Example 1. The homogeneous dispersion was then used to make a dressing using a mould with V-shaped grooves in an analogous manner to that described in the first production example. However, in this case, drying was carried out at 100° C. for 30 minutes. FIGS. 2b to 2d are analogous to FIGS. 1b to 1d. The dressing thus produced was also packaged as described in the first production example. In use, it was found that this dressing had good haemostatic properties.

Following the procedure described in the first production example above, homogeneous dispersions were made up having the compositions set out below.

| 1) Protanal LF10/60 (1) | 8% | 2) Blanose 7HOFD (2) | 5% |
| --- | --- | --- | --- |
| Propylene Glycol | 4% | Glycerol | 10% |
| Glycerol | 20% | Propylene Glycol | 3% |
| H$_2$O | 68% | H$_2$O | 82% |
| 3) Natrosol 250 HX | | 4) Courlose P40BP (5) | 6% |
| Pharm (3) | 4% | Glycerol | 14% |
| PEG 400 (4) | 12% | Propylene Glycol | 4% |
| H$_2$O | 84% | H$_2$O | 76% |

-continued

| | | | | | |
|---|---|---|---|---|---|
| 5) Natrosol 250HX | | | 6) Protanal, LF10/60 (1) | | 5% |
| Pharm (3) | 4% | | C/YSF (6) | | 1% |
| Sorbitol | 4% | | Glycerol | | 10% |
| Glycerol | 10% | | PEG 200 (7) | | 5% |
| H$_2$O | 82% | | H$_2$O | | 79% |
| 7) Natrosol 250 HX | | | 8) Natrosol 250 HX | | |
| Pharm (3) | 4% | | Pharm (3) | | 4% |
| Glycerol | 10% | | Glycerol | | 5% |
| Propylene Glycol | 2% | | Propylene Glycol | | 1% |
| H$_2$O | 84% | | H$_2$O | | 90% |
| 9) Natrosol 250 HX | | | 10) Natrosol 250 HX | | |
| Pharm (3) | 4% | | Pharm (3) | | 4% |
| Glycerol | 13% | | Sorbitol | | 12% |
| Propylene Glycol | 3% | | H$_2$O | | 84% |
| H$_2$O | 80% | | | | |
| 11) Protanal LF10/60 (1) | 5% | | 12) Akucell AF2201 (8) | | 5% |
| C/YSF (5) | 1% | | Glycerol | | 10% |
| Glycerol | 20% | | Propylene Glycol | | 2% |
| PEG 200 (7) | 10% | | H$_2$O | | 83% |
| H$_2$O | 64% | | | | |
| 13) Natrosol 250 HX | | | 14) Akucell AF2201 (8) | | 5% |
| Pharm (3) | 4% | | Glycerol | | 27% |
| Glycerol | 15% | | Propylene Glycol | | 8% |
| Propylene Glycol | 5% | | H$_2$O | | 60% |
| H$_2$O | 76% | | | | |
| 15) Courlose P40BP (5) | 5% | | 16) Blanose 7HOFD (2) | | 5% |
| Glycerol | 27% | | Glycerol | | 27% |
| Propylene Glycol | 8% | | Propylene Glycol | | 8% |
| H$_2$O | 60% | | H$_2$O | | 60% |

(1) Protan LF10/60 is sodium alginate supplied by Protanal Limited
(2) Blanose 7HOFD is a sodium carboxymethyl cellulose having a viscosity of 1500 to 2800 mPa · s (1% solution at 25° C.) and a degree of substitution of 0.65 to 1.45 molecules per glucose unit, supplied by Aqualon (U.K.) Limited.
(3) Natrosol 250 HX Pharm is a hydroxyethyl cellulose having a molecular weight of about 1.5 MD, a viscosity of 1500 to 2800 mPa · s (1% solution at 25° C.) and a degree of substitution of about 2.5 molecules per glucose unit, supplied by Aqualon (U.K.) Limited.
(4) PEG 400 is polyethylene glycol having a molecular weight of about 400.
(5) Courlose P40BP is a sodium carboxymethyl cellulose having a viscosity of 30 to 56 mPa · s (1% solution at 25° C.) and a degree of substitution of 0.7 to 0.85 molecules per glucose unit, supplied by Courtaulds Chemicals Limited.
(6) C/YSF is calcium alginate supplied by Kelco Limited
(7) PEG 200 is polyethylene glycol having a molecular weight of about 200.
(8) Akucell AF2201 is a sodium carboxymethyl cellulose having a viscosity of 300 to 500 mPa · s (1% solution at 25° C.) and a degree of substitution of 0.8 to 0.95 molecules per glucose unit, supplied by AKZO Industrial Colloids Limited.

Each of the above homogeneous dispersions was poured into one of the two moulds referred to above and was dried using one of the sets of conditions set out below.

| Oven | Temperature | Time (minutes) |
|---|---|---|
| Conventional | 60° C. | 80 |
| Conventional | 100° C. | 30 |
| Fan-assisted | 60° C. | 40 |
| Fan-assisted | 140° C. | 5 |
| 650W microwave | — | 3 |

In the case of dispersions 1 to 11, a non-tacky web dressing was produced. In the case of dispersion 12, the web dressing produced was lightly tacky on one side but not on the other. Dispersions 13 to 16 produced web dressings which were lightly tacky on both surfaces.

The web dressings made from dispersions 1 to 16 were all useful in treating both exuding and non-exuding wounds.

It will be appreciated that the present invention has been described above purely by way of illustration and that variations and modifications, as will be apparent to those skilled in the art, can be made without departing from the scope of the invention.

What is claimed is:

1. A dressing consisting of a non-reinforced, apertured gel web, wherein the gel is substantially anhydrous and comprises a water-soluble, polysaccharide- or cellulosic-polymer and a humectant, and wherein the web is sufficiently soluble in wound fluid and saline so as to sufficiently dissolve therein and be substantially washed from a wound when said wound is heavily exudating or when said wound is irrigated with saline.

2. The dressing of claim 1, which is lightly tacky.

3. The dressing of claim 1, wherein the apertures in the dressing are square.

4. The dressing of claim 1, wherein the depth of the gel between the apertures varies, and wherein each element of the web has a U-shaped or a V-shaped cross section.

5. The dressing of claim 1, wherein the water soluble polymer is a hydroxyethylcellulose, carboxymethyl cellulose or water soluble sodium or potassium alginate.

6. The dressing of claim 1, wherein the humectant is glycerol, sorbitol, propylene glycol, a low molecular weight polyethylene glycol or a low molecular weight polypropylene glycol.

7. The dressing of claim 1, wherein the humectant comprises a mixture of glycerol and propylene glycol.

8. The dressing of, wherein the gel comprises from 2 to 8 parts by weight of humectant or mixture of humectant, for each part by weight of water-soluble polymer.

9. The dressing of claim 1, wherein the gel further comprises a medicament or an additive; povidone iodine; a quaternary ammonium salt; silver sulphur diazine; a local anesthetic; a growth factor; an enzyme; a glycosaminoglycan; or a matrix protein.

10. The dressing of claim 1, which contains a buffering agent.

11. A method for producing a non-reinforced apertured dressing which comprises:

preparing an aqueous solution comprising a water-soluble, polysaccharide- or cellulosic-polymer and a humectant;

applying the solution to a mould comprising a pattern of interconnected grooves surrounding a plurality of upstanding bosses; and drying the solution in the mould to form the dressing.

\* \* \* \* \*